United States Patent [19]

Neirinckx

[11] Patent Number: 4,990,327
[45] Date of Patent: Feb. 5, 1991

[54] DESENSITIZING DENTAL COMPOSITION

[76] Inventor: Rudi D. Neirinckx, 20 Elm Close, Amersham, Buckinghamshire, United Kingdom

[21] Appl. No.: 76,932
[22] PCT Filed: Nov. 7, 1986
[86] PCT No.: PCT/GB86/00690
 § 371 Date: Aug. 18, 1987
 § 102(e) Date: Aug. 18, 1987
[87] PCT Pub. No.: WO87/02890
 PCT Pub. Date: May 21, 1987

[30] Foreign Application Priority Data

Nov. 13, 1985 [GB] United Kingdom ............... 8527962

[51] Int. Cl.$^5$ ..................... A61K 7/16; A61K 7/18
[52] U.S. Cl. ........................... 424/52; 424/49; 222/94

[58] Field of Search .............. 424/49, 52; 222/94

[56] References Cited

U.S. PATENT DOCUMENTS 3,122,483  2/1964  Rosenthal ............... 424/49
4,083,955  4/1978  Grabenstetter ........... 424/49
4,098,435  7/1978  Weyn ................... 222/94

FOREIGN PATENT DOCUMENTS 1552119  9/1976  United Kingdom .

Primary Examiner—Ronald W. Griffin
Attorney, Agent, or Firm—Browdy and Neimark

[57] ABSTRACT

A dental desensitizing two-phase composition wherein one phase contains physiologically acceptable strontium ion and the second phase contains physiologically acceptable fluoride ion. The two phases are mixed when used.

12 Claims, 3 Drawing Sheets

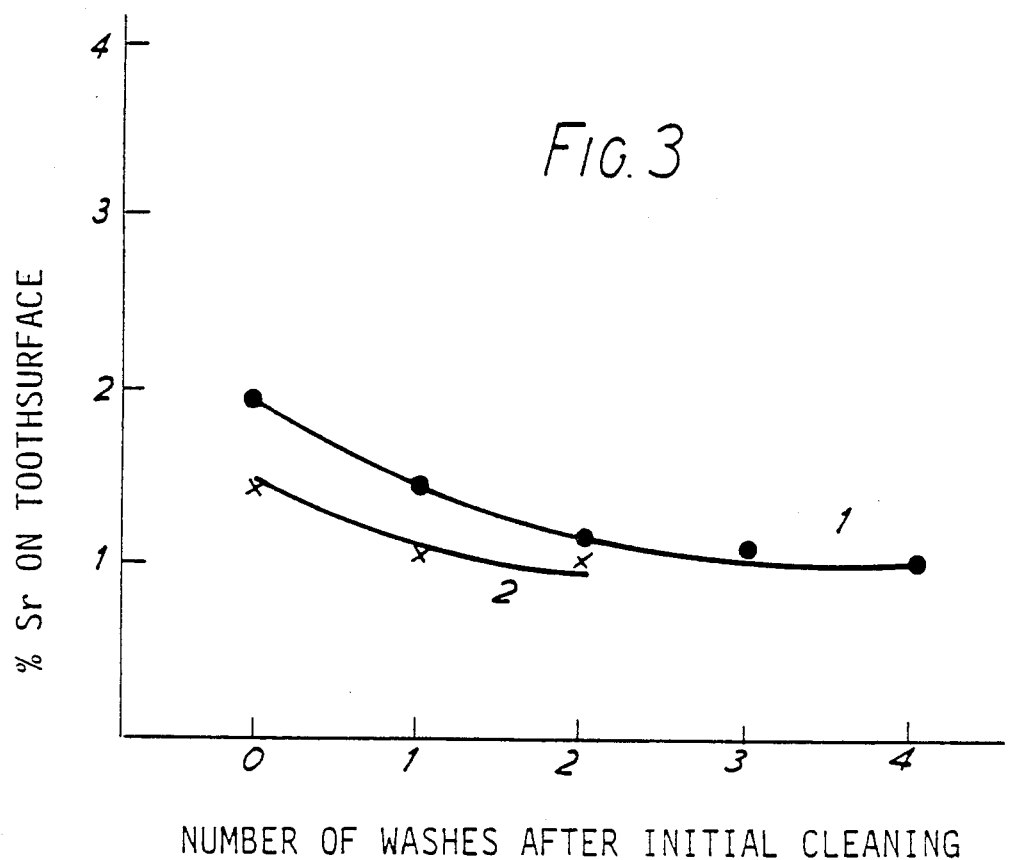
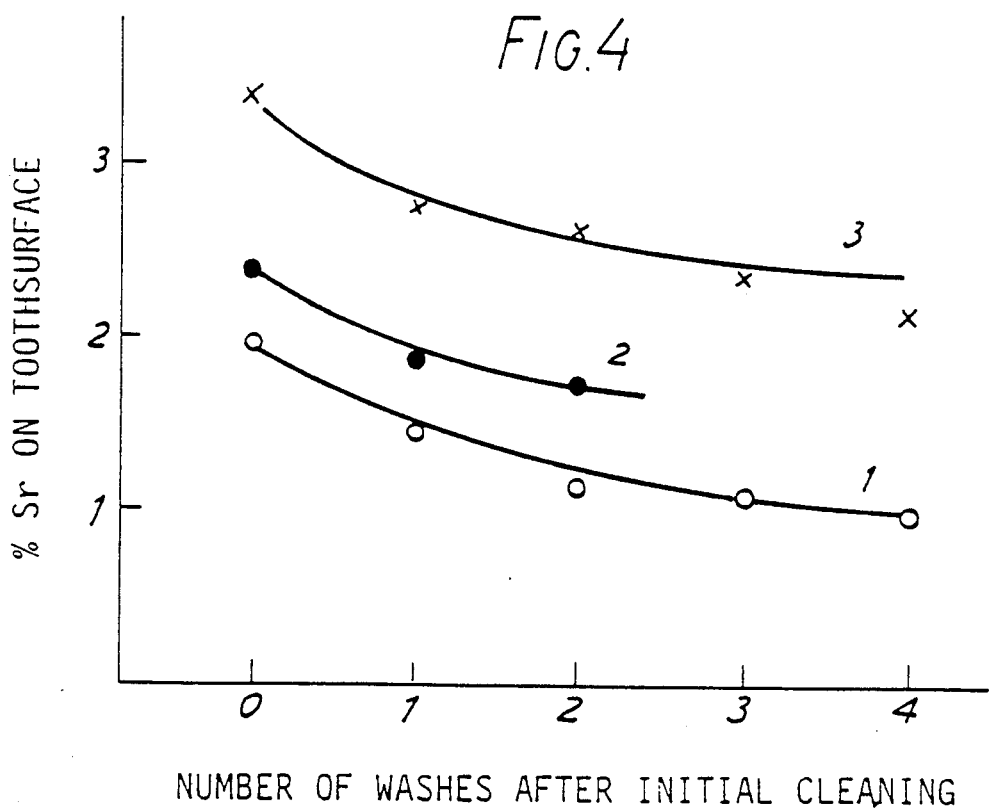

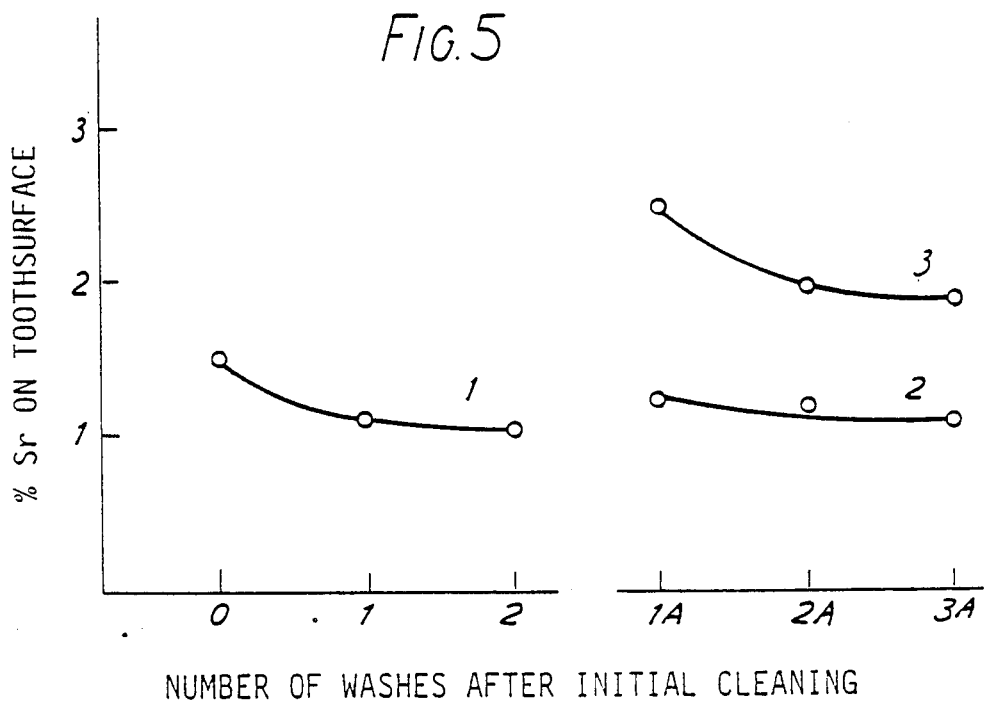
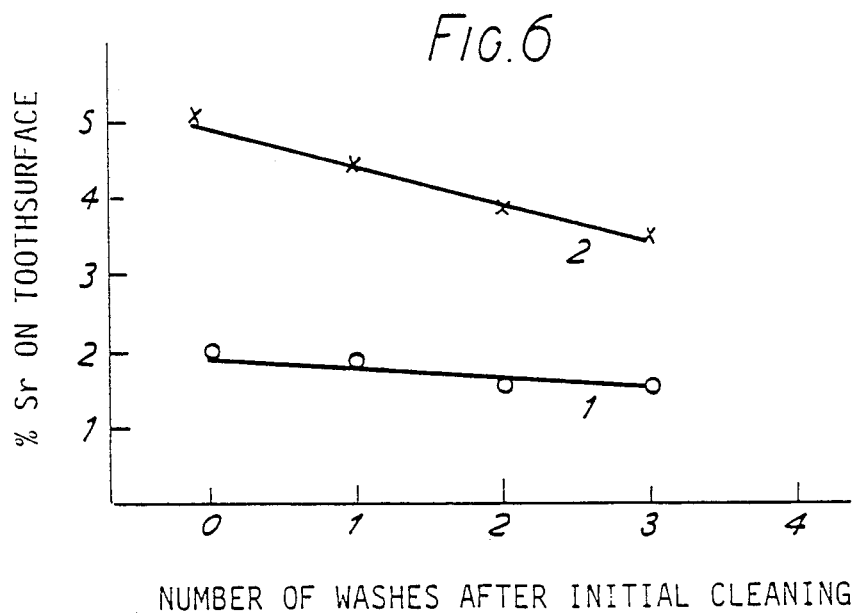

DESENSITIZING DENTAL COMPOSITION

BACKGROUND OF THE INVENTION

This invention relates to a desensitizing dental composition and more particularly to a two-component desensitizing dental composition.

Hypersensitivity is a common phenomenon among dental patients that often causes the patient to reject dental treatment. The sensitivity may be local or general and very often complicates treatment of a variety of dental problems. Treatment of hypersensitivity has resulted in varying degrees of success. These treatments often have relied upon astringent or coagulating effects of various agents, occulating properties or the ability to render calcium less soluble. Examples of these agents include fluoride, formaldehyde, silver nitrate, zinc oxide and strontium chloride.

Strontium chloride has been shown to be particularly effective in its desensitizing effect. However, strontium chloride is highly soluble in aqueous solution so that when presented to the teeth as an aqueous solution, it is not particularly effective since it has a higher affinity for water rather than the surface of the teeth. In order to be effective, the strontium must penetrate the tooth surface. It has also been proposed to combine strontium chloride with a physiologically acceptable source of fluoride since the fluoride has been shown to be effective in preventing or minimizing cavity formation in teeth. However, attempts to form mixtures including a source of strontium and a source of fluoride have proven ineffective as a means for delivering both strontium and a fluoride to the teeth since they readily precipitate to form strontium fluoride and, as a precipitate, are ineffective to penetrate the tooth surface to provide the desired dental effect.

It has been proposed in Canadian Patent No. 907,514 to Stearns et al to provide a dental desensitizing composition including a source of fluoride and a source of strontium which is complexed with a chelating agent such as ethylenediamine tetraacetic acid in order to prevent precipitation of strontium chloride so that, upon use, the fluoride and the strontium area available separately to the tooth surface to allow penetration into the tooth for their desired effects. However, the chelating agent to which strontium is complexed renders it much more difficult to deposit onto the tooth surface as compared to strontium ion per se. The chelating agent greatly inhibits the insitu reaction of strontium and fluoride which must occur on the tooth surface in order to allow deposition of both on the tooth surface, thereby to effect tooth desensitization.

Accordingly, it would be highly desirable to provide a dental desensitizing composition which is a source of both strontium and fluoride both of which are in the form which permits ease of their penetration into or adherence onto the tooth in order to attain the desired dental effect. Accordingly, it would be desirable to provide a dental desensitizing composition wherein strontium fluoride formation is minimized before the time the composition is applied to the teeth and wherein the strontium ion remains uncomplexed so that it can easily penetrate the surface of the teeth when applied directly to the teeth.

SUMMARY OF THE INVENTION

In accordance with this invention, there is provided a system for preparing a desensitizing composition comprising strontium and fluoride, said system comprising a source of first and second compositions said compositions being segregated and containing respectively a physiologically acceptable source of free strontium ions and a physiologically acceptable source of free fluoride ions and dispensing means arranged to dispense said compositions so that a mixture thereof may be formed on or immediately prior to application thereof to the teeth.

More specifically the invention provides a package is provided which houses a dental desensitizing composition which includes a physiologically acceptable source of strontium ion and a physiologically acceptable source of fluoride ion wherein the physiologically acceptable source of strontium ion and the physiologically acceptable source of fluoride ion are maintained separate from each other and are not admixed until application to the teeth is desired. When admixed on the teeth, the resultant mixture contains both free strontium ion and free fluoride ion.

This mixture interacts with the teeth and both components are more rapidly immobilized on the teeth surface because of the presence of both components initially in the uncomplexed free ion form.

It has been found that by operating in this manner, the compositions of this invention are far more effective than compositions which contain strontium ion chemically bound to a chelating agent or bound to fluoride in the form of strontium fluoride.

The package may include compartments, one for housing the strontium ion in the absence of fluoride ion and another for housing fluoride in the absence of strontium ion. Each of the strontium and fluoride ions then can be dispensed simultaneously on the teeth surfaces.

A method also is provided for treating a patient having a dental hypersensitivity by depositing both ions on the teeth surfaces and mixing the ions directly on the teeth surfaces.

The invention further provides a kit for densitizing the dental area of a patient having hypersensitive teeth which comprises supplies of two separate dentifrice or mouthwash compositions, one of said compositions containing a source of a physiologically acceptable free strontium ion and the other of said compositions containing a physiologically acceptable source of free fluoride ion, and optionally instructions for admixing said phases on or immediately prior to application to the teeth of the patient to form on the surface of the teeth strontium and fluoride in a form to effect desensitization of the dental area of the patient.

The use of a physiologically acceptable source of fluoride to produce industrially a kit or system for the treatment of teeth in a combination therapy involving the application of strontium ions and fluoride ions using separate compositions containing strontium ions and fluoride ions forms a further aspect of the invention, as does the use of a physiologically acceptable source of strontium to produce industrially a kit or system for the treatment of teeth in a combination therapy involving the application of strontium ions and fluorine ions using separate compositions containing strontium ions and fluorine ions.

BRIEF DESCRIPTION OF THE DRAWINGS

FIGS. 3–6 illustrate graphically the results of experiments carried out to demonstrate the efficacy of the invention.

DESCRIPTION OF SPECIFIC EMBODIMENTS

Figure 1:
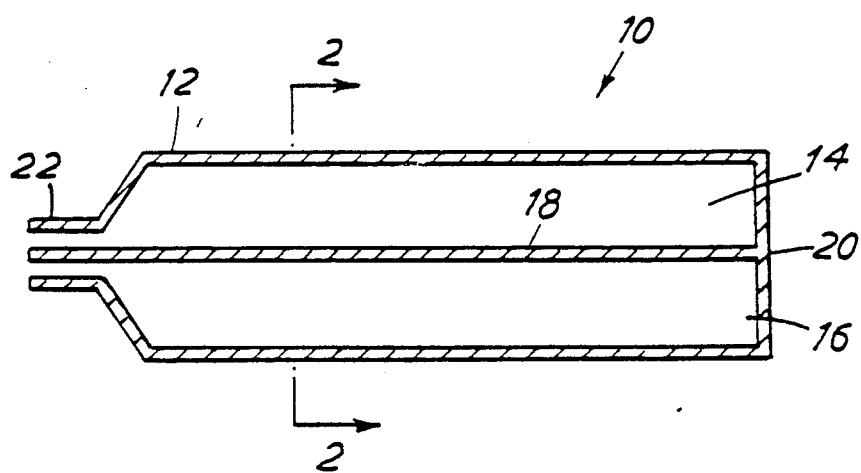
FIG. 1 is a cross-sectional side view of a dispenser suitable for use in carrying out the present invention.
Figure 2:
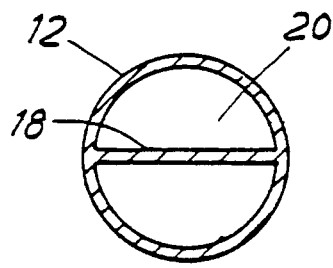
FIG. 2 is a cross-sectional view taken along line 2—2 of FIG. 1.

The present invention is useful in any topically applied dental desensitizing composition including toothpastes, mouthwashes or the like. The physiologically acceptable source of strontium ion is maintained in a phase of the composition separate from a phase containing the physiologically acceptable source of fluoride ion.

Any convenient means for effecting the separation can be utilized. For example, a single container can be compartmentalized so that the strontium containing phase and the fluoride containing phase are housed in separate compartments and are not admixed until applied to the teeth. Alternatively, the strontium containing phase and the fluoride containing phase can be housed in separate containers from which the respective phases are dispensed for admixture just prior to use.

Thus for example, in one embodiment said segregated compositions are housed in a common container and are separated from one another by a barrier which prevents mixing prior to the compositions being dispensed. The barrier may comprise a wall integrally formed with said container or it may comprise a physiologically acceptable composition which is adapted to be dispensed from said container with said segregated compositions.

Applicant's invention is based upon the discovery that when a source of fluoride and a source of strontium which have been maintained separate from each other are combined for the first time on the surface of the teeth, a synergistic effect is obtained as a result of interaction of strontium and fluoride on or close to the tooth surface, leading to better strontium uptake by the teeth in preference to dissolution in the aqueous medium from which it is derived and before the conversion of strontium into less-active forms, such as strontium fluoride precipitate, which removes both components from availability to the teeth. When both components are added simultaneously to the teeth the desensitizing is thus enhanced. If the fluoride and the strontium were to be applied separately, the desired synergistic effect would not occur or would occur only to an insignificant extent as a result, for example, of the natural level of the other component in saliva, the drinking water or on the tooth surface. Since this is typically much lower than the proposed levels the densitizing effect is much smaller.

When the strontium and the fluoride are housed in a manner allowing premature admixture, undesirable precipitation of strontium fluoride occurs so that much lower levels of the free components are available for adsorption by the teeth.

Furthermore, if either the strontium ion or the fluoride ion is complexed, the formation of the reaction product of strontium and fluoride is significantly reduced but the rate of deposition of strontium on the teeth is also so reduced as to adversely affect its densensitization property. For example, when strontium is complexed with a chelating agent such as EDTA, precipitation by fluoride is inhibited, but the strontium is also rendered very water-soluble so that is does not interact effectively with the teeth.

Representative suitable sources of physiologically acceptable fluoride ion include sodium fluoride, potassium fluoride, lithium fluoride, zinc fluoride, ammonium fluoride, rubidium fluoride, potassium bifluoride, ammonium bifluoride, sodium silicofluoride, mixtures thereof or the like. The fluoride ion is contained in the fluoride-containing phase at a concentration between about 0.001% and about 4% preferably between about 0.02% and about 2%. In order to maintain the fluoride in the form which permits its subsequent penetration into the tooth, the pH of the fluoride-containing composition is maintained between 3 and about 9, preferably between about 5 and about 8. It is preferred to utilize acidified monofluorophosphate for fluoride because it is safe and easily releases fluoride when in an aqueous medium.

Representative suitable sources of strontium include strontium chloride, strontium nitrate, strontium acetate, strontium bromide, strontium iodide, strontium bromate, strontium perchlorate, strontium formate, strontium lactate, mixtures thereof or the like. The strontium-containing phase is maintained at a pH of between about 3 and about 7, preferably between about 5 and 7 so that the strontium ion is solubilized within the strontium ion-containing phase. The strontium is present in the strontium-containing phase at a concentration between about 0.1% and about 12%, preferably between about 8% and 12%. The preferred source of strontium is strontium chloride since it is readily dissolved in an aqueous medium.

It is of course desirable that said strontium containing composition is substantially free of free fluoride and said fluoride-containing composition is substantially free of free strontium.

The strontium and the fluoride are most conveniently maintained in a viscous aqueous medium such as in the form of a gel or a paste. It is most preferred that the strontium and the fluoride be present in either a toothpaste composition suitable for cleaning teeth, in a mouthwash with desensitizing properties, or in a gel composition of the type commonly employed by dentists in order to apply treatment compositions to the teeth or gum surface. The toothpaste compositions typically contain water, a foaming agent such as sodium lauryl phosphate, a small proportion of abrasive particles such as silicates, carbonate or dehydrated silica gels, flavors and sweeteners.

When it is desirable to form the strontium-containing phase and the fluoride-containing phase as a gel, an aqueous solution of the strontium or the fluoride is admixed with a pharmaceutically acceptable gelling agent such as sodium carboxymethyl cellulose, hydroxyethyl cellulose, hydroxypropyl cellulose, magnesium aluminium silicate, silica gel or the like. The thixotropic properties of the resultant gel can be varied by varying the concentration of the gelling agent with increased concentrations providing increased thixotropic properties as is well known in the art. When it is desired to form the strontium-containing phase and the fluoride-containing phase as aqueous solutions as could be used as a mouthwash, separate aqueous solutions of strontium and fluoride may for example be enclosed in a two-compartment bottle from which both solutions can be dispensed simultaneously immediately prior to use as a mouthwash.

The compositions utilized in the present invention are conveniently formed by first preparing an aqueous solution of either the strontium compound or the fluoride compound, preferably in deionized water. The concentration of the strontium compound is such that in the final composition it comprises between about 0.1 and about 12 weight percent of the final composition (exclusive of the fluoride-containing composition), preferably between about 8 and about 12 weight percent. Similarly, the fluoride-containing composition in the aqueous solution should be such that the concentration of the fluoride in the final composition is between about 0.001 and about 4 weight percent (exclusive of the strontium-containing phase), preferably between about 0.02 and about 4 weight percent. After the aqueous solution has been formed, the conventional agents utilized to form a paste or a gel or the like may then be admixed with the aqueous solution to form the final composition.

Referring to FIGS. 5 and 6, a suitable container 10 useful in the present invention comprises an outer wall formed of a flexible material such as a polymer which can contain a sheet of flexible metal such as aluminium 12. The container 10 is segmented into two compartments 14 and 16 by means of wall 18 which is sealed to the interior surface of the outer wall 12. One end 20 of the container 10 is sealed while the opposing end 22 is open so that it can be conveniently opened or closed in a conventional manner such as with a screw cap (not shown). Compartment 14 can house either the strontium phase of the fluoride phase while the other compartment 16 can house the phase not housed within compartment 14. It is to be understood that the strontium-containing phase and the fluoride-containing phase can be housed in separate containers from which they can be conveniently dispensed just prior to being topically applied to the dental area of the user. Alternatively, an intermediate layer of toothpaste, gel or the like containing neither strontium nor fluoride can be interposed between the strontium layer and the fluoride layer with in the same container so that mixture of the strontium layer and the fluoride layer does not occur until use.

The following examples illustrates the present invention and are not intended to limit the same.

EXAMPLE 1

In Vivo Tests

A layer of a commercially available fluoride toothpaste and a layer of a commercially available strontium chloride containing toothpaste were dispensed simultaneously. The concentrations used were 10% $SrCl_2.6H_2O$ in one toothpaste and 1.23% acidulated phosphate fluoride in the other toothpaste.

Mixing was obtained by brushing the two layers directly on the teeth of each patient. Each patient was treated at the 4 quadrants of the mouth. One quadrant was treated with the layered $Sr^2+.2F$ toothpaste preparation; one quadrant was treated with a $Sr^2+.2F$ containing toothpaste only; one quadrant was treated with the acidulated phosphate fluoride toothpaste only; while one quadrant was untreated (blank). The procedure was carried out daily on 12 patients for a total period of up to 6 months. All patients reported some relief in the mixture quadrant, with some reporting no relief in any quadrants. Generally, a significant improvement over the results obtained with either one of the toothpastes used singly was reported subjectively by the patients.

EXAMPLE 2

In Vitro Tests

Experiments were carried out to measure the uptake of radioactive strontium by tooth enamel from strontium-containing compositions in the presence and absence of simultaneously applied fluoride-containing compositions.

2.1 Toothpaste Compositions

In a first series of experiments a strontium-containing toothpaste containing 10% by weight of $SrCl_2$ was used as the strontium-containing composition and a fluoride-containing toothpaste containing 0.76% by weight of sodium monfluorophosphate was used at the fluoride containing composition.

The following treatment regime was used:
1. Groups of three extracted teeth were brushed with the toothpaste(s) for 1 minute each.
2. An initial cleaning was carried out by rinsing thoroughly with tap water.
3. The radioactivity of the teeth was measured.
4. The teeth were washed again with tap water.
5. The radioactivity of the teeth was measured again.
6. The percentage uptake of strontium was calculated and expressed as a fraction of the strontium present in 100 mg of toothpaste.

A. The dependency of strontium uptake on the amount of strontium-containing paste was assessed by applying to each tooth either 100 or 300 mg of labelled toothpaste.

The results are illustrated in FIG. 3 in which Line 1 shows the results of using 100 mg of toothpaste and Line 2 shows the results of using 300 mg of toothpaste. It can be seen that the uptake of strontium is virtually independent of the amount of strontium-containing toothpaste used, provided that sufficient is present to cover the tooth surface. More specifically the total uptake of labelled strontium on the tooth surface was practically the same when 100 and 300 mg of toothpaste were used. This indicates that the uptake of strontium is presumably a surface phenomenum during the first minute of application.

B. The effect of mixing a strontium-containing toothpaste with a fluoride containing toothpaste was investigated by mixing varying amounts of the two toothpastes in situ. The results are summarised in FIG. 4 in which Line 1 shows the results of using the strontium-containing toothpaste alone, Line 2 shows the results of using 3 parts of strontium-containing toothpaste with 1 part of fluoride-containing toothpaste and Line 3 shows the results of using equal amounts of the two toothpastes.

It can be seen from FIG. 4 that by mixing the strontium and fluoride immediately prior to application to the tooth surface there is a synergistic effect with the uptake of strontium unexpectedly being potentiated by the addition of fluoride.

C. Experiments were carried out to determine whether the uptake of strontium by tooth enamel was enhanced by a second application of strontium-containing toothpaste to the same teeth and what the effect was of simultaneously applying a fluoride-containing toothpaste. The results are summarised in FIG. 5 in which Line 1 shows the uptake of strontium when using a strontium-containing toothpaste alone, Line 2 shows the effect of an additional brushing with a strontium-containing toothpaste and Line 3 shows the strontium uptake when a mixture of strontium toothpaste and fluoride toothpaste is used for the second application. (In FIG. 5 the points 1A, 2A and 3A represent the washes after the second application).

It can be seen that additional strontium uptake resulting from a further treatment with a strontium-containing toothpaste is enhanced by the presence of fluoride (Line 3) compared to Line 2 where no fluoride is used.

2.2 Mouthwash Compositions

In a second series of experiments a liquid mouthwash composition was prepared by instantaneous mixing 20 seconds before use of a aqueous solution of radioactively labelled strontium (0.2% $SnCl_2.6H_2O$ by weight) and an aqueous solution of 0.2% NaF. The tests were carried out by equilibrating teeth with the mixture.

The results are summarised in FIG. 6 where Line 1 illustrates the percent saturation uptake from 5 ml of the strontium chloride solution per tooth surface and Line 2 illustrates the result of using the mixed $NaF/SrO_2$ solution. A significant enhancement of strontium uptake occurred when the mixed solution was used.

I claim:

1. A system for preparing a desensitizing composition effective in producing an enhanced desensitizing effect comprising strontium and fluoride, said system comprising a source of first and second compositions, said compositions being segregated and containing respectively a physiologically acceptable source of free strontium ions and a physiologically acceptable source of free fluoride ions, and dispensing means arranged to dispense said compositions so that a mixture thereof may be formed on or immediately prior to application thereof to the teeth.

2. A system according to claim 1 wherein said segregated compositions are housed in a common container and are separated from one another by a barrier which prevents mixing prior to the compositions being dispensed.

3. A system according to claim 1 wherein the source of strontium ion is strontium chloride.

4. A system according to claim 1 wherein the source of fluoride ion is acidulated phosphate fluoride.

5. A system according to claim 1 wherein each of said segregated compositions is in the form of a paste or a gel.

6. A system according to claim 1 wherein each of the said segregated compositions is in the form of a liquid solution.

7. A system according to claim 1 wherein said strontium compound is present in a concentration of between about 0.1% and about 12%.

8. A system according to claim 1 wherein the concentration of fluoride compound is between about 0.001% and about 4%.

9. A kit for producing an enhanced desensitizing effect in the dental area of a patient having hypersensitive teeth which comprises supplies of two separate dentifrice or mouthwash compositions, one of said compositions containing a source of a physiologically acceptable free strontium ion and the other of said compositions containing a physiologically acceptable source of free fluoride ion.

10. A kit according to claim 9 further comprising instructions for admixing said phases on or immediately prior to application to the teeth of the patient to form on the surface of the teeth strontium and fluoride in a form to effect desensitization of the dental area of the patient.

11. A method for obtaining an enhanced desensitizing effect in a subject suffering from dental sensitivity comprising providing a source of first and second compositions, said compositions being segregated and containing respectively a physiologically acceptable source of free strontium ions and a physiologically acceptable source of free fluoride ions, dispensing said compositions and applying a mixture thereof to the teeth of said subject, said mixture being formed on or immediately prior to application thereof to the teeth.

12. A method for providing an enhanced desensitizing effect in a subject suffering from dental sensitivity, comprising:
   providing a dispenser having a first compartment containing a first composition and a second compartment containing a second composition, said first and second compartments being segregated so that said first and second compositions do not intermix prior to dispensing thereof, said first composition comprising a physiologically acceptable source of free strontium ions and said second composition comprising a physiologically acceptable source of free fluoride ions; and
   dispensing said first and second compositions onto the teeth of said subject and effecting mixing of said first and second compositions on or immediately prior to application thereof to the teeth.

* * * * *